US00PP33595P2

(12) United States Plant Patent
Head et al.

(10) Patent No.: US PP33,595 P2
(45) Date of Patent: Nov. 2, 2021

(54) ***ILEX* PLANT NAMED 'RLH-IO-1'**

(50) Latin Name: *Ilex opaca*
Varietal Denomination: RLH-IO-1

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: Head's Select, Inc., Seneca, SC (US)

( * ) Notice: Subject to any disclaimer, the term of this patent is extended or adjusted under 35 U.S.C. 154(b) by 0 days.

(21) Appl. No.: 17/120,152

(22) Filed: Dec. 12, 2020

(51) Int. Cl.
*A01H 5/12* (2018.01)
*A01H 6/00* (2018.01)

(52) U.S. Cl.
USPC ..... Plt./247
CPC ..... *A01H 6/00* (2018.05)

(58) Field of Classification Search
USPC ..... Plt./247
CPC ..... A01H 5/00; A01H 5/12
See application file for complete search history.

*Primary Examiner* — Kent L Bell
(74) *Attorney, Agent, or Firm* — C. Anne Whealy

(57) ABSTRACT

A new and distinct *Ilex* plant named 'RLH-IO-1', characterized by its low-growing to spreading/trailing and mounding plant habit; vigorous growth habit and moderate growth rate; moderately freely branching habit; strong and flexible lateral branches that resist cracking, breakage and splitting; dark green-colored leaves that are initially bright green when developing; color is maintained throughout the year in full or partial sunlight conditions; and good garden performance, winter hardiness and tolerance to stresses, pathogens and pests common to *Ilex* plants.

1 Drawing Sheet

Botanical designation: *Ilex opaca.*
Cultivar denomination: 'RLH-1O-1'.

STATEMENT REGARDING PRIOR DISCLOSURES BY INVENTORS/APPLICANTS

The Inventors/Applicants assert that no publications nor advertisements relating to sales, offers for sale or public distribution occurred more than one year prior to the effective filing date of this application. Any information about the claimed plant would have been obtained from a direct or indirect disclosure from the Inventors/Applicants. Inventors/Applicants claim a prior art exemption under 35 U.S.C. 102(b)(1) for disclosure and/or sales prior to the filing date but less than one year prior to the effective filing date.

BACKGROUND OF THE INVENTION

The present Invention relates to a new and distinct *Ilex* plant, botanically known as *Ilex opaca*, commonly referred to as American Holly and hereinafter referred to by the name 'RLH-IO-1'.

The new *Ilex* plant originated from an open-pollination of *Ilex opaca* 'IOJD-1', a proprietary cultivar and not patented, as the female, or seed, parent with an unknown selection of *Ilex opaca*, as the male, or pollen, parent. The new *Ilex* plant was discovered and selected by the Inventors in 1990 as a single plant within the progeny of the stated open-pollination in a controlled environment in Long Creek, Oconee County, S.C.

Asexual reproduction of the new *Ilex* plant by semi-hardwood and hardwood stem cuttings in Long Creek, Oconee County, S.C. since 2000 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'RLH-IO-1'. These characteristics in combination distinguish 'RLH-IO-1' as a new and distinct *Ilex* plant:

1. Low-growing to spreading/trailing and mounding plant habit; suitable as a ground cover, trained to arbors or to cascade over walls.
2. Vigorous growth habit and moderate growth rate.
3. Moderately freely branching habit.
4. Strong and flexible lateral branches that resist cracking, breakage and splitting.
5. Dark green-colored leaves that are initially bright green when developing; color is maintained throughout the year in full or partial sunlight conditions.
6. Good garden performance, winter hardiness and tolerance to stresses, pathogens and pests common to *Ilex* plants.

Plants of the new *Ilex* differ primarily from plants of the female parent, 'IOJD-1', in the following characteristics:

1. Plants of the new *Ilex* have a low-growing to spreading/trailing and mounding plant habit whereas plants of 'IOJD-1' have an upright to mounding and pendulous plant habit.

2. Leaves of plants of the new *Ilex* are undulate and rugose whereas leaves of plants of 'IOJD-1' are flat and rugulose.
3. Plants of the new *Ilex* only produce male flowers whereas plants of 'IOJD-1' only produce female flowers.

Plants of the new *Ilex* can be compared to the plants of *Ilex opaca* 'Maryland Dwarf', not patented. In side-by-side comparisons, plants of the new *Ilex* differ from plants of 'Maryland Dwarf' in the following characteristics:

1. Plants of the new *Ilex* have a low-growing to spreading/trailing and mounding plant habit whereas plants of 'Maryland Dwarf' are compact and have an upright and mounding plant habit typical of many Holly species.
2. Plants of the new *Ilex* are more vigorous and faster growing than plants of 'Maryland Dwarf'.
3. Plants of the new *Ilex* have strong and flexible lateral branches that resist cracking, breakage and splitting whereas plants of 'Maryland Dwarf' have stiff and rigid lateral branches that are prone to splitting.
4. Leaves of plants of the new *Ilex* are undulate and rugose whereas leaves of plants of 'Maryland Dwarf' are flat to slightly cupped and rugulose.
5. Leaves of plants of the new *Ilex* maintain their dark green coloration throughout the year under full or partial sunlight conditions whereas leaves of plants of 'Maryland Dwarf' become yellow green in color during the winter when grown under full sun conditions.
6. Plants of the new *Ilex* only produce male flowers whereas plants of 'Maryland Dwarf' only produce female flowers.

BRIEF DESCRIPTION OF THE PHOTOGRAPH

The accompanying colored photograph illustrates the overall appearance of the new *Ilex* plant. The photograph shows the colors as true as it is reasonably possible to obtain in colored reproductions of this type. Colors in the photograph may differ slightly from the color values cited in the detailed botanical description which accurately describe the colors of the new *Ilex* plant. The photograph is a side perspective view of a typical plant of 'RLH-IO-1' grown in an outdoor nursery.

DETAILED BOTANICAL DESCRIPTION

The aforementioned photograph and following observations and measurements describe plants grown during the summer in an outdoor nursery in Seneca, S.C. and under cultural practices typical of commercial *Ilex* production. During the production of the plants, day temperatures ranged from −5° C. to 45° C., night temperatures ranged from ranged from −25° C. to 35° C. and grown under full and partial sunlight conditions. Plants were 30 years old when the photograph was taken and 15 years old when the detailed description was taken. In the following description, color references are made to The Royal Horticultural Society Colour Chart, 2007 Edition, except where general terms of ordinary dictionary significance are used.

Botanical classification: *Ilex opaca* 'RLH-IO-1'.

Parentage:

*Female, or seed, parent.*—*Ilex opaca* 'IOJD-1', a proprietary cultivar and not patented.

*Male, or pollen, parent.*—Unknown selection of *Ilex opaca*, not patented.

Propagation:

*Type.*—By semi-hardwood and hardwood stem cuttings.

*Time to initiate roots, summer.*—About 45 to 60 days at temperatures about 25° C. to 30° C.

*Time to initiate roots, winter.*—About 60 to 90 days at temperatures about 15° C. to 22° C.

*Time to produce a rooted young plant, summer.*—About 80 to 120 days at temperatures about 25° C. to 30° C.

*Time to produce a rooted young plant, winter.*—About 100 to 150 days at temperatures about 16° C. to 25° C.

*Root description.*—Fine to medium in thickness, fibrous; typically white in color, close to 155C and becoming closer to 199C with development; actual color of the roots is dependent on substrate composition, water quality, fertilizer, substrate temperature and physiological age of roots.

*Rooting habit.*—Freely branching; dense.

Plant description:

*Plant and growth habit.*—Perennial evergreen shrub; low-growing to spreading/trailing and mounding plant habit; suitable as a ground cover or can be trained to arbors or to cascade over and cover walls; vigorous growth habit and moderate growth rate.

*Branching habit.*—Moderately freely branching habit; branching pattern is deliquescent.

*Plant height.*—About 70 cm.

*Plant diameter, area of spread.*—About 250 cm.

*Lateral branch description.*—Length: About 3 cm to 15 cm. Diameter: About 1.5 mm to 2.5 mm. Internode length: About 1 cm to 3.5 cm. Strength: Strong and flexible; resistant to cracking, breakage and splitting. Aspect: Outward to reclining, trailing and cascading. Texture: Initially, slightly puberulent becoming woody and glabrous with development. Color, developing: Close to 145B. Color, developed: Close to 199C.

*Leaf description.*—Arrangement: Alternate, simple. Length: About 6 cm to 10 cm. Width: About 3 cm to 6 cm. Shape: Oval to rotund; undulate and slightly twisted. Apex: Subacute with a single sharp spine. Base: Obtuse. Margin: Shallowly lobed with six to seven sharp spines on each side of the leaf; undulate. Spine length: About 1 mm to 2 mm. Spine color: Close to N144D. Venation pattern: Pinnate. Texture and luster, upper surface: Rugose, glabrous; coriaceous; glossy. Texture and luster, lower surface: Rugose, mostly glabrous with pubescence along midvein; semi-glossy. Color: Developing leaves, upper surface: Close to between 143A and 144A. Developing leaves, lower surface: Close to 146C to 146D. Fully expanded leaves, upper surface: Close to 139A; venation, close to 139B. Fully expanded leaves, lower surface: Close to 146B to 146C; venation, close to 146C. Petioles: Length: About 6 mm to 10 mm. Diameter: About 1.5 mm to 1.8 mm. Texture, upper and lower surfaces: Minute lanulose pubescence, coriaceous. Color, upper surface: Close to 139B. Color, lower surface: Close to 146C.

Flower description:

*Flower appearance and arrangement.*—Small staminate (male) cruciform flowers are arranged in axillary compound cymes; freely flowering with numerous cymes developing per plant, cymes with typically about two to twelve flowers; flowers face mostly outwardly.

*Natural flowering season*.—Plants flower in mid to late spring in South Carolina; flowers last about five to seven days on the plant; flowers are not persistent.

*Fragrance*.—Faintly fragrant; honey-like.

*Cyme diameter*.—About 1 cm to 1.5 cm.

*Cyme height*.—About 1 cm to 2 cm.

*Flower diameter*.—About 7.5 mm to 8 mm.

*Flower length* (*height*).—About 3.5 mm to 4 mm.

*Flower buds*.—Length: About 2 mm to 3 mm. Diameter: About 2 mm to 3 mm. Shape: Spherical to ovoid. Color: Close to NN155B.

*Petals*.—Quantity and arrangement: About four in a single whorl and fused at the base. Length: About 3 mm to 4 mm. Width: About 2.5 mm to 3 mm. Shape: Obelliptic to obovate. Apex: Obtuse, rounded. Base: Fused. Margin: Entire. Texture, upper and lower surfaces: Smooth, glabrous. Color: When opening, upper and lower surfaces: Close to NN155A. Fully opened, upper and lower surfaces: Close to NN155B; color becoming closer to 155C with development.

*Sepals*.—Quantity and arrangement: About four in a single whorl and fused at the base. Length: About 1.5 mm to 1.8 mm. Diameter: About 1.5 mm to 1.8 mm. Shape: Deltoid. Apex: Acute to subacute. Base: Fused. Margin: Entire. Texture, upper and lower surfaces: Scabrous. Color, upper and lower surfaces: Close to 144A.

*Peduncles*.—Length: About 4.5 mm to 9 mm. Diameter: About 0.7 mm to 0.8 mm. Aspect: Outwardly, about 45° from stem axis. Strength: Moderately strong. Texture: Slightly pubescent. Color: Close to 144A; in full sunlight conditions becoming tinged with close to 166A.

*Pedicels*.—Length: About 2 mm to 6 mm. Diameter: About 0.3 mm to 0.7 mm. Aspect: Outwardly. Strength: Moderately strong. Texture: Slightly pubescent. Color: Close to 144A.

*Reproductive organs*.—Androecium: Quantity per flower: About four. Filament length: About 1.75 mm to 2 mm. Filament color: Close to NN155B. Anther length: About 2 mm to 2.25 mm. Anther shape: Rotund to ovate. Anther color: Close to 150D. Pollen amount: Moderate. Pollen color: Close to 150D. Gynoecium: To date, only staminate flowers have been observed on plants of the new *Ilex*.

Garden performance: Plants of the new *Ilex* have been observed to have good garden performance and to be tolerant to rain, wind and temperatures ranging from about −25° C. to about 45° C.

Pathogen tolerance: Plants have been observed to be tolerant to Leaf Spot (*Cylindrocladium* spp.). Plants have not been observed to be tolerant to other pathogens common to *Ilex* plants.

It is claimed:

1. A new and distinct *Ilex* plant named 'RLH-IO-1' as illustrated and described.

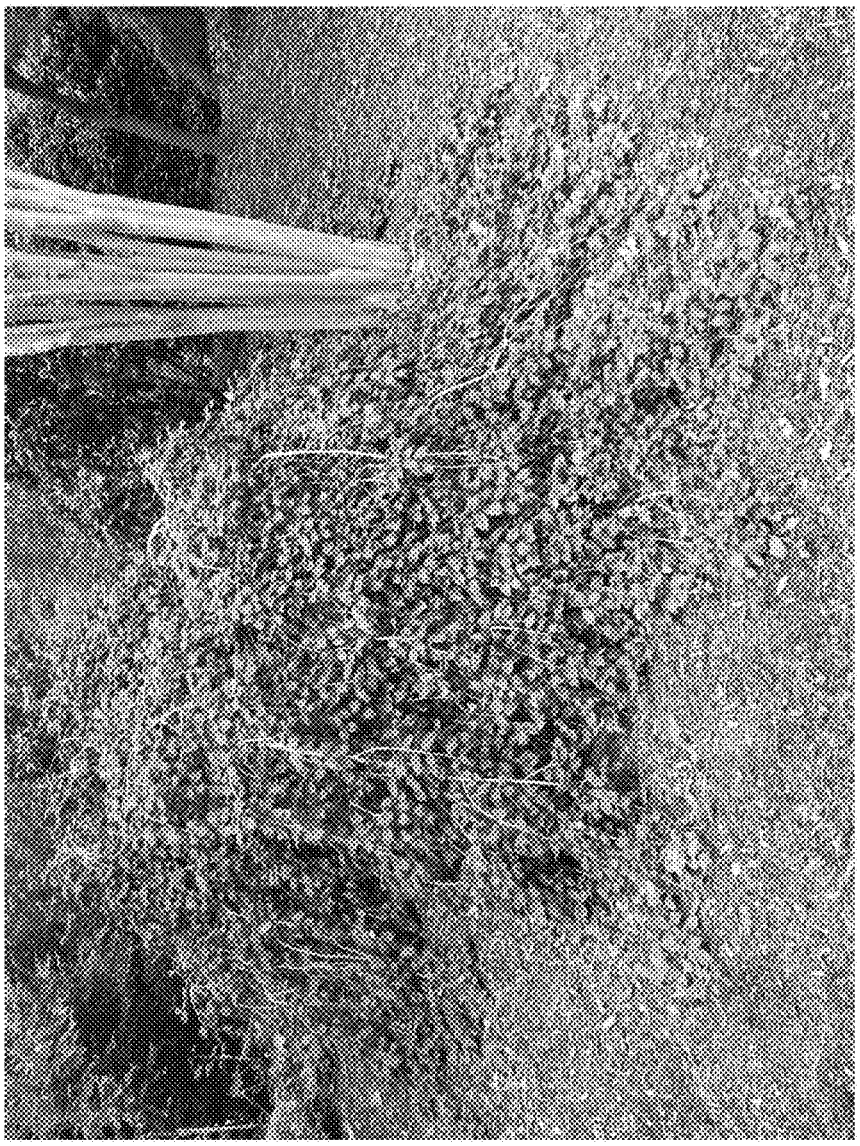

* * * * *